(12) United States Patent
Davila et al.

(10) Patent No.: US 12,171,183 B2
(45) Date of Patent: Dec. 24, 2024

(54) HYBRID PEPPER VARIETY 'VP18090009'

(71) Applicant: Axia Vegetable Seeds Group, Inc., Woodland, CA (US)

(72) Inventors: Jesus Saldivar Davila, Culiacan (MX); Bharath K. Reddy, Woodland, CA (US); Magda Karina, Culiacan (MX)

(73) Assignee: AXIA VEGETABLE SEEDS GROUP, INC., Woodland, CA (US)

( * ) Notice: Subject to any disclaimer, the term of this patent is extended or adjusted under 35 U.S.C. 154(b) by 216 days.

(21) Appl. No.: 17/698,741

(22) Filed: Mar. 18, 2022

(65) Prior Publication Data

US 2022/0295732 A1 Sep. 22, 2022

Related U.S. Application Data (60) Provisional application No. 63/163,553, filed on Mar. 19, 2021.

(51) Int. Cl.
*A01H 6/82* (2018.01)
*A01H 5/08* (2018.01)

(52) U.S. Cl.
CPC .............. *A01H 6/822* (2018.05); *A01H 5/08* (2013.01)

(58) Field of Classification Search
None
See application file for complete search history.

(56) References Cited

U.S. PATENT DOCUMENTS 10,575,482 B2 * 3/2020 Berke .................... A01H 6/822

* cited by examiner

*Primary Examiner* — Cathy Kingdon Worley
(74) *Attorney, Agent, or Firm* — Morrison & Foerster LLP (57) ABSTRACT A new pepper hybrid designated as 'VP18090009' is disclosed. 'VP18090009' is a hot pepper variety of the jalapeno type exhibiting stability and uniformity. Variety 'VP18090009' produces extra-large fruits that are green prior to maturity and red at maturity. Additionally, variety 'VP18090009' has a desirable growth habit and plant height that result in high numbers of flowers and fruit.

15 Claims, 5 Drawing Sheets
(5 of 5 Drawing Sheet(s) Filed in Color)

HYBRID PEPPER VARIETY 'VP18090009'

CROSS-REFERENCE TO RELATED APPLICATION

This application claims the benefit of U.S. Provisional Application No. 63/163,553, filed Mar. 19, 2021, which is hereby incorporated by reference in its entirety.

FIELD

The present disclosure relates to the field of plant breeding. In particular, the present disclosure relates to a new and distinctive Jalapeno-type hot pepper, Capsicum annuum L., variety designated 'VP18090009'.

BACKGROUND

Peppers (Capsicum spp.) are members of the nightshade family (Solanaceae) and are important crop species in a variety of cultures. Though they originated in the tropical regions of the Americas, they are now grown and utilized globally as vegetables, spices, and medicines. Several species of the genus Capsicum are cultivated, with Capsicum annum L. being the most commonly grown pepper in the United States. Capsicum annuum L. comprises many varieties that can be divided into two broad groups: hot peppers and sweet peppers. The fruits of hot peppers produce capsaicin, resulting in a pungent (hot) flavor, while the fruits of sweet peppers produce little to no capsaicin, resulting in a non-pungent (mild) flavor.

In temperate regions, pepper plants are grown as herbaceous annuals; in warmer regions where temperatures do not drop below freezing, they may be grown as perennials. Pepper plants may have a variety of growth habits, including erect, compact, or prostrate. They may exhibit determinate growth, with stems eventually terminating in flowers, or indeterminate growth, with stems continuously producing flowers without terminating. The leaves, which may take a variety of shapes from broadly ovate to ovate lanceolate, are shiny and glabrous and arranged alternately on the stem. The root system will form a deep taproot if uninjured, a secondary root system spreading laterally downward, and some adventitious roots at the soil surface. The flowers are white and develop either singly or in small clusters of two or three as the plant grows. The flowers may self-pollinate or be pollinated by insects, allowing for cross-pollination. The fruits may be a wide variety of shapes and colors at maturity, and are usually green prior to maturity, except for white and purple varieties which maintain the same color throughout growth and ripening. The seeds are kidney-shaped and develop on the interior surface of the hollow fruit flesh.

Since their export from Central America by Europeans, hot pepper varieties of Capsicum annum L. have become a particularly valuable class of pepper in a wide variety of cuisines, including those of Latin America, East and South Asia, and Africa. In the United States, the market for hot peppers has shown considerable growth in recent years. Hot peppers may be eaten raw or cooked, and may be processed into chili powders, salsas, and hot sauces. The capsaicin that gives these peppers their unique pungent flavor is produced at the stem end of the fruit and diffuses into the whole of the fruit, and can be found in high concentrations in the placental tissue surrounding the seeds. The amount of capsaicin in fruits can vary widely between hot pepper varieties based on genetics and cultivation environment. Hot peppers have been the subject of breeding efforts globally, and many varieties have been produced with a variety of shapes, colors, and capsaicin levels. Given the global demand for hot peppers and their increasing popularity in the United States, breeders also strive to produce new hot pepper varieties with improved yield, pepper size, and plant vigor.

Therefore, there is a continued need for new and unique hot pepper varieties. In particular, there is a need for indeterminate varieties which exhibit vigorous growth and continuous production of flowers resulting in high yields.

BRIEF SUMMARY

In order to meet these needs, the present disclosure is directed to improved pepper varieties.

In one aspect, the present disclosure is directed to a hybrid pepper, Capsicum annuum L., seed designated as 'VP18090009' having ATCC Accession Number PTA-127283. In an embodiment of this aspect, the present disclosure is directed to a Capsicum annuum L. pepper plant and parts isolated therefrom produced by growing 'VP18090009' pepper seed. In another embodiment of this aspect, the present disclosure is directed to a Capsicum annuum L. plant and parts isolated therefrom having all the physiological and morphological characteristics of a Capsicum annuum L. plant produced by growing 'VP18090009' pepper seed having ATCC Accession Number PTA-127283. In still another embodiment of this aspect, the present disclosure is directed to a method of making pepper seed, the method comprising crossing a 'VP18090009' pepper plant with another pepper plant and harvesting seed therefrom.

Pepper plant parts include pepper leaves, shoots, stems, roots, cuttings, flowers, ovules, pollen, seeds, pepper fruits, parts of pepper fruits, cells, cotyledons, hypocotyls, meristems, and the like. In one embodiment, the present disclosure is further directed to a leaf, an ovule, a pollen grain, a fruit, or a cell isolated from 'VP18090009' pepper plants. In a further embodiment of this aspect, the present disclosure is directed to a fruit isolated from 'VP18090009' pepper plants. In certain embodiments, the present disclosure is further directed to pollen or ovules isolated from 'VP18090009' pepper plants. In another embodiment, the present disclosure is further directed to protoplasts produced from 'VP18090009' pepper plants. In another embodiment, the present disclosure is further directed to tissue or cell culture of 'VP18090009' pepper plants, and to pepper plants regenerated from the tissue or cell culture, wherein the plants have all of the morphological and physiological characteristics of 'VP18090009' pepper plants. In certain embodiments, tissue culture of 'VP18090009' pepper plants is produced from a plant part selected from root, root tip, meristematic cell, stem, hypocotyl, petiole, cotyledon, leaf, flower, anther, pollen, pistil, and fruit.

In a further aspect, the present disclosure is directed to a method of producing a seed of a 'VP18090009'-derived pepper plant, including the steps of: (a) crossing a pepper plant of the variety designated as 'VP18090009', representative sample of seed having been deposited under ATCC Accession Number PTA-127283, with itself or a second pepper plant; and (b) whereby seed of a 'VP18090009'-derived pepper plant to form. In another embodiment of this aspect, the method further includes the steps of: (c) crossing a plant grown from 'VP18090009'-derived pepper seed with itself or a second pepper plant to yield additional 'VP18090009'-derived pepper seed; (d) growing the additional 'VP18090009'-derived pepper seed of step (c) to yield additional 'VP18090009'-derived pepper plants; and (e)

repeating steps (c) and (d) for an additional 3-10 generations to generate further 'VP18090009'-derived pepper plants.

In yet another aspect, the present disclosure is directed to a method of vegetatively propagating a plant of hybrid pepper 'VP18090009', the method including the steps of: (a) collecting tissue capable of being propagated from a plant of hybrid pepper 'VP18090009', representative sample of seed having been deposited under ATCC Accession Number PTA-127283; (b) cultivating the tissue to obtain proliferated shoots; and (c) rooting the proliferated shoots to obtain rooted plantlets. In a further embodiment of this aspect, the method further includes step (d) growing plants from the rooted plantlets. In another embodiment, the present disclosure is further directed to pepper plants, plant parts and seeds produced by the pepper plants where the pepper plants are produced by any of the preceding methods of the disclosure.

In another embodiment, the present disclosure is directed to single gene converted plants of hybrid pepper 'VP18090009'. The single transferred gene may preferably be a dominant or recessive allele. Preferably, the single transferred gene will confer such trait as sex determination, herbicide resistance, insect resistance, resistance for bacterial, fungal, or viral disease, improved harvest characteristics, enhanced nutritional quality, or improved agronomic quality. The single gene may be a naturally occurring pepper gene or a transgene introduced through genetic engineering techniques.

In addition to the exemplary aspects and embodiments described above, further aspects and embodiments will become apparent by reference by study of the following descriptions.

BRIEF DESCRIPTION OF THE DRAWINGS

The patent or application file contains at least one drawing executed in color. Copies of this patent or patent application publication with color drawings will be provided by the office upon request and payment of the necessary fee.

FIG. 1A shows flowers of hybrid pepper 'VP18090009'.

FIG. 1B shows flowers of pepper variety 'Mixteco'.

FIGS. 3A-3B show fruit of hybrid pepper 'VP18090009'.

FIGS. 4A-4B show a comparison of the plant height and fruit load of upper shoots of hybrid pepper 'VP18090009' with those of pepper variety 'Mixteco'.

DETAILED DESCRIPTION

There are numerous steps in the development of novel, desirable pepper germplasm. Plant breeding begins with the analysis of problems and weaknesses of current pepper germplasms, the establishment of program goals, and the definition of specific breeding objectives. The next step is selection of germplasm that possess the traits to meet the program goals. The goal is to combine in a single variety or hybrid an improved combination of desirable traits from the parental germplasm. These important traits may include higher yield, field performance, and resistance to diseases and insects. These important traits may also include fruit and agronomic quality such as fruit shape, fruit appearance, fruit size, and fruit capsaicin levels.

Choice of breeding or selection methods can depend on the mode of plant reproduction, the heritability of the trait(s) being improved, and the type of variety used commercially (e.g., $F_1$ hybrid variety, pureline variety, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable variety. This approach has been used extensively for breeding disease-resistant varieties. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program may include a periodic, objective evaluation of the efficiency of the breeding procedure. Evaluation criteria vary depending on the goal and objectives, and can include gain from selection per year based on comparisons to an appropriate standard, the overall value of the advanced breeding lines, and the number of successful varieties produced per unit of input (e.g., per year, per dollar expended, etc.).

Promising advanced breeding lines may be thoroughly tested and compared to appropriate standards in environments representative of the commercial target area(s) for at least three years. The best lines can then be candidates for new commercial varieties. Those still deficient in a few traits may be used as parents to produce new populations for further selection. These processes, which lead to the final step of marketing and distribution, may take from ten to twenty years from the time the first cross or selection is made.

One goal of pepper plant breeding is to develop new, unique, and genetically superior pepper varieties. A breeder can initially select and cross two or more parental lines, followed by repeated selfing and selection, producing many new genetic combinations. Moreover, a breeder can generate multiple different genetic combinations by crossing, selfing, and mutations. A plant breeder can then select which germplasms to advance to the next generation. These germplasms may then be grown under different geographical, climatic, and soil conditions, and further selections can be made during, and at the end of, the growing season.

The development of commercial pepper varieties thus requires the development of parental pepper varieties, the crossing of these varieties, and the evaluation of the crosses. Pedigree breeding and recurrent selection breeding methods may be used to develop varieties from breeding populations. Breeding programs can be used to combine desirable traits from two or more varieties or various broad-based sources into breeding pools from which new varieties are developed by selfing and selection of desired phenotypes. The new varieties are crossed with other varieties and the hybrids from these crosses are evaluated to determine which have commercial potential.

Pedigree breeding is generally used for the improvement of self-pollinating crops or inbred lines of cross-pollinating crops. Two parents which possess favorable, complementary traits are crossed to produce an $F_1$. An $F_2$ population is produced by selfing one or several $F_1$s or by intercrossing two $F_1$s (sib mating). Selection of the best individuals is usually begun in the $F_2$ population. Then, beginning in the $F_3$, the best individuals in the best families are selected. Replicated testing of families, or hybrid combinations involving individuals of these families, often follows in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new varieties.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding may be used to transfer genes for a simply inherited, highly heritable trait into a desirable homozygous cultivar or line that is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

In addition to phenotypic observations, the genotype of a plant can also be examined. There are many laboratory-based techniques known in the art that are available for the analysis, comparison and characterization of plant genotype. Such techniques include, without limitation, DNA- or RNA-sequencing, CAPS Markers, ELISA, Western blot, microarrays, Single Nucleotide Polymorphisms (SNPs), Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), Differential Display Polymerase Chain Reaction (DD-PCR), Quantitative Real-Time Polymerase Chain Reaction (qRT-PCR), DNA Amplification Fingerprinting (DAF), Sequence Characterized Amplified Regions (SCARs), Amplified Fragment Length Polymorphisms (AFLPs), and Simple Sequence Repeats (SSRs, which are also referred to as Microsatellites).

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select toward the genome of the recurrent parent and against the markers of the donor parent. This procedure attempts to minimize the amount of genome from the donor parent that remains in the selected plants. It can also be used to reduce the number of crosses back to the recurrent parent needed in a backcrossing program. The use of molecular markers in the selection process is often called genetic marker enhanced selection or marker-assisted selection. Molecular markers may also be used to identify and exclude certain sources of germplasm as parental varieties or ancestors of a plant by providing a means of tracking genetic profiles through crosses.

Mutation breeding may also be used to introduce new traits into pepper varieties. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation (such as X-rays, Gamma rays, neutrons, Beta radiation, or ultraviolet radiation), chemical mutagens (such as base analogs like 5-bromo-uracil), antibiotics, alkylating agents (such as sulfur mustards, nitrogen mustards, epoxides, ethyleneamines, sulfates, sulfonates, sulfones, or lactones), azide, hydroxylamine, nitrous acid, or acridines. Once a desired trait is observed through mutagenesis the trait may then be incorporated into existing germplasm by traditional breeding techniques. Details of mutation breeding can be found in *Principles of Cultivar Development* by Fehr, Macmillan Publishing Company (1993).

The production of double haploids can also be used for the development of homozygous varieties in a breeding program. Double haploids are produced by the doubling of a set of chromosomes from a heterozygous plant to produce a completely homozygous individual. For example, see Wan, et al., *Theor. Appl. Genet.*, 77:889-892 (1989).

Additional non-limiting examples of breeding methods that may be used include, without limitation, those found in *Principles of Plant Breeding*, John Wiley and Son, pp. 115-161 (1960); Allard (1960); Simmonds (1979); Sneep, et al. (1979); Fehr (1987); and *Genetics, Genomics and Breeding of Peppers and Eggplants*, Kang & Kole, CRC Press (2013).

Definitions

In the description that follows, a number of terms are used. In order to provide a clear and consistent understanding of the specification and claims, including the scope to be given such terms, the following definitions are provided:

Backcrossing. Backcrossing is a process in which a breeder repeatedly crosses hybrid progeny back to one of the parents, for example, a first generation hybrid $F_1$ with one of the parental genotypes of the $F_1$ hybrid.

Essentially all the physiological and morphological characteristics. A plant having essentially all the physiological and morphological characteristics means a plant having the physiological and morphological characteristics of the recurrent parent, except for the characteristics derived from the converted gene.

Gene. As used herein, "gene" refers to a segment of nucleic acid. A gene can be introduced into a genome of a species, whether from a different species or from the same species, using transformation or various breeding methods.

Hot pepper. As used herein, "hot pepper" refers to a pepper plant, or fruits thereof, that produce fruit containing sufficient capsaicin to produce a pungent flavor.

Internode. As used herein, "internode" refers to a segment of the stem between nodes.

Pepper fruit. As used herein, a "pepper fruit" is a fruit produced by a *Capsicum annuum* L. plant and is commonly referred to as a pepper. The color of a pepper fruit can be green, red, yellow, orange and, more rarely, white, black, and brown, depending on when they are harvested and the specific cultivar.

Pepper Mild Mottle Virus (PMMoV). A type of Tobamovirus that can affect plants of *Capsicum annuum* L. Symptoms may include chlorosis, stunting, and distortion of flower and fruit structures.

Potato Virus Y (PVY). A virus of the Potyviridae family that affects plants of the nightshade family, including pepper plants. Symptoms include mottling, vein banding, vein clearing, and distortion of the leaves, stunting, and necrosis of stems.

Propagate. To "propagate" a plant means to reproduce the plant by means including, but not limited to, seeds, cuttings, divisions, tissue culture, embryo culture or other in vitro method.

Pungent. As used herein, "pungent" refers to the unique flavor characteristic of pepper fruits which contain capsaicin, often described as "hot" or "spicy". The pungency of hot peppers may vary between varieties depending upon the amount of capsaicin present in the fruit.

Regeneration. As used herein, "regeneration" refers to the development of a plant from tissue culture.

Single gene converted. As used herein, "single gene converted" or "conversion plant" refers to plants which are developed by a plant breeding technique called backcrossing wherein essentially all of the desired morphological and physiological characteristics of an inbred are recovered in addition to the single gene transferred into the inbred via the backcrossing technique or via genetic engineering.

Sweet pepper. As used herein, "sweet pepper" refers to a pepper plant, or fruits thereof, that lack sufficient capsaicin to produce a pungent flavor.

Tobamovirus. A genus of virus affecting diverse plant species, including *Capsicum annuum* L. Symptoms may include systemic chlorosis, systemic necrosis, and defoliation.

Tobacco Mosaic Virus (TMV). A type of Tobamovirus that can affect plants of *Capsicum annuum* L. Symptoms may include chlorosis, curling, distortion, and stunting of the leaves and flowers.

Overview of the Hybrid Pepper Variety 'VP18090009'

Figure 1A:
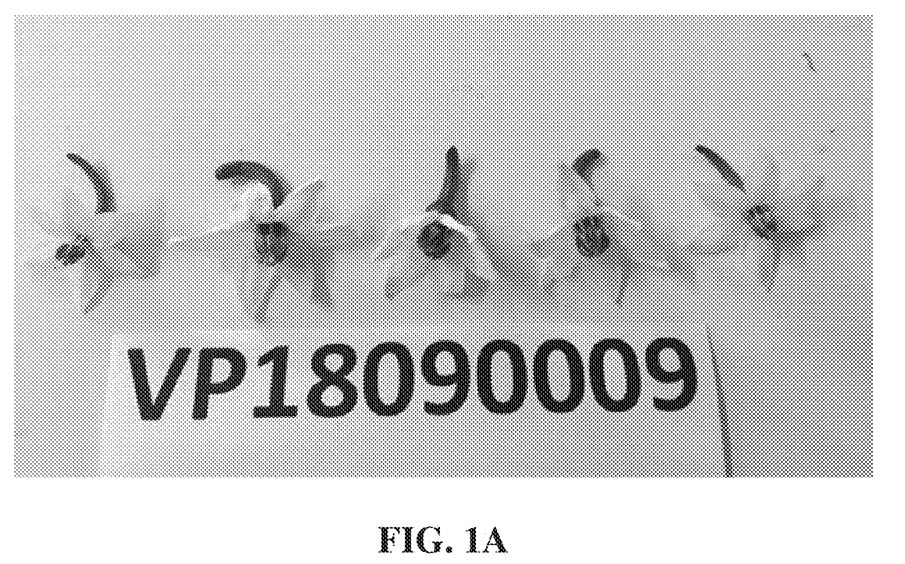
FIGS. 1A-1B show a comparison of the flowers of hybrid pepper 'VP18090009' with those of pepper variety 'Mixteco'.
Figure 2:
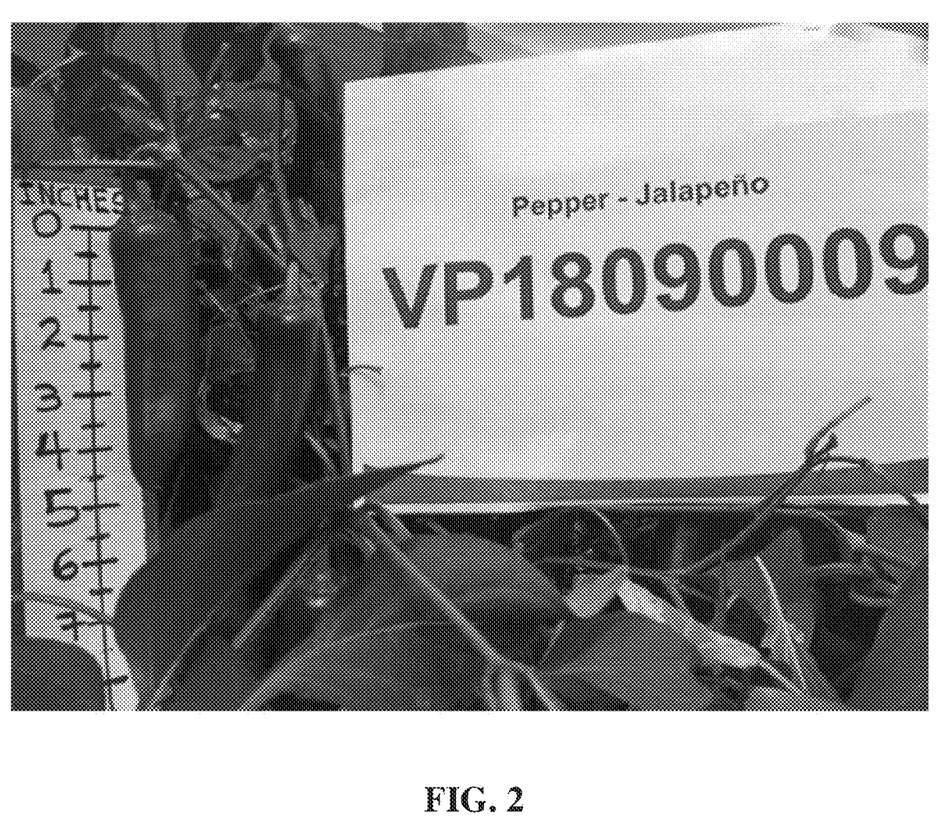
FIG. 2 shows the upper shoot of a plant of hybrid pepper 'VP18090009' ("PANTERA") with fruit.
Figure 3A:
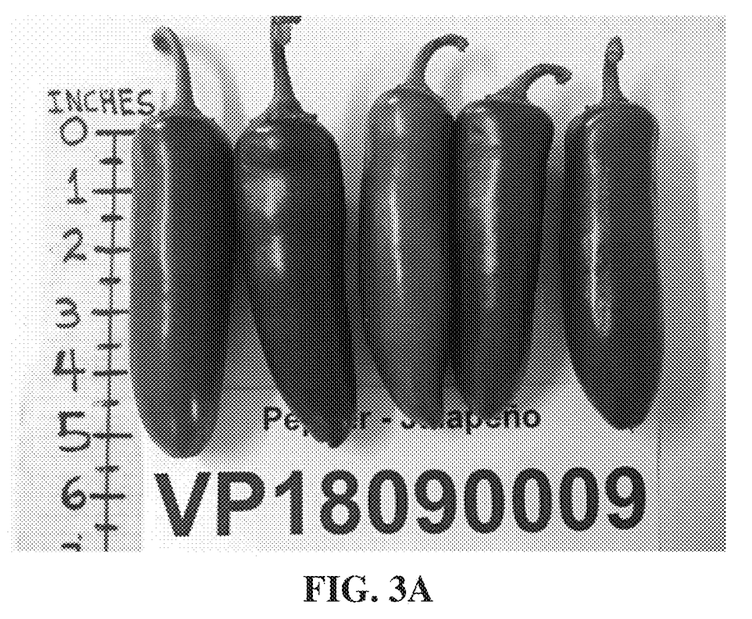
FIG. 3A shows immature fruit of hybrid pepper 'VP18090009'.
Figure 3B:
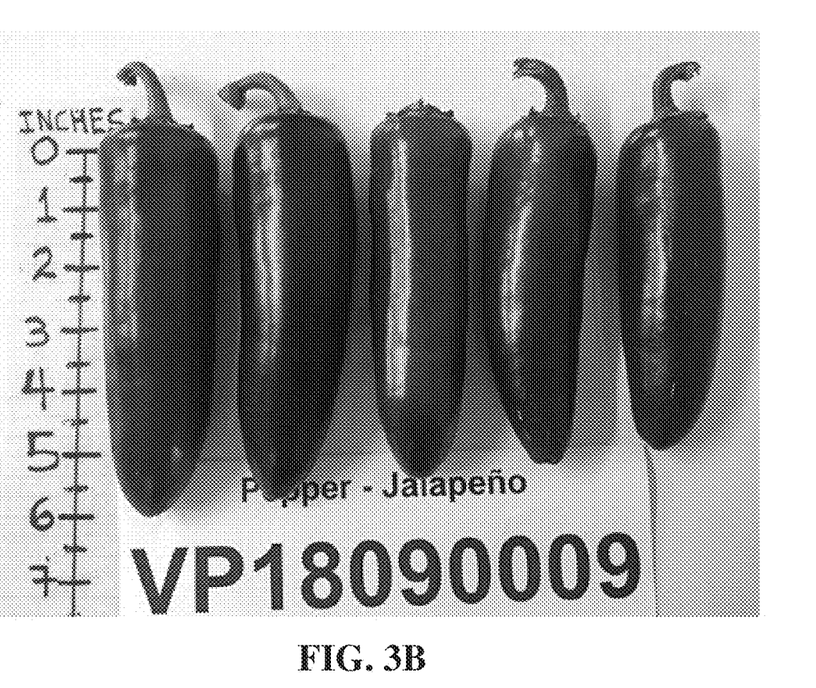
FIG. 3B shows mature fruit of hybrid pepper 'VP18090009'.
Figure 4A:
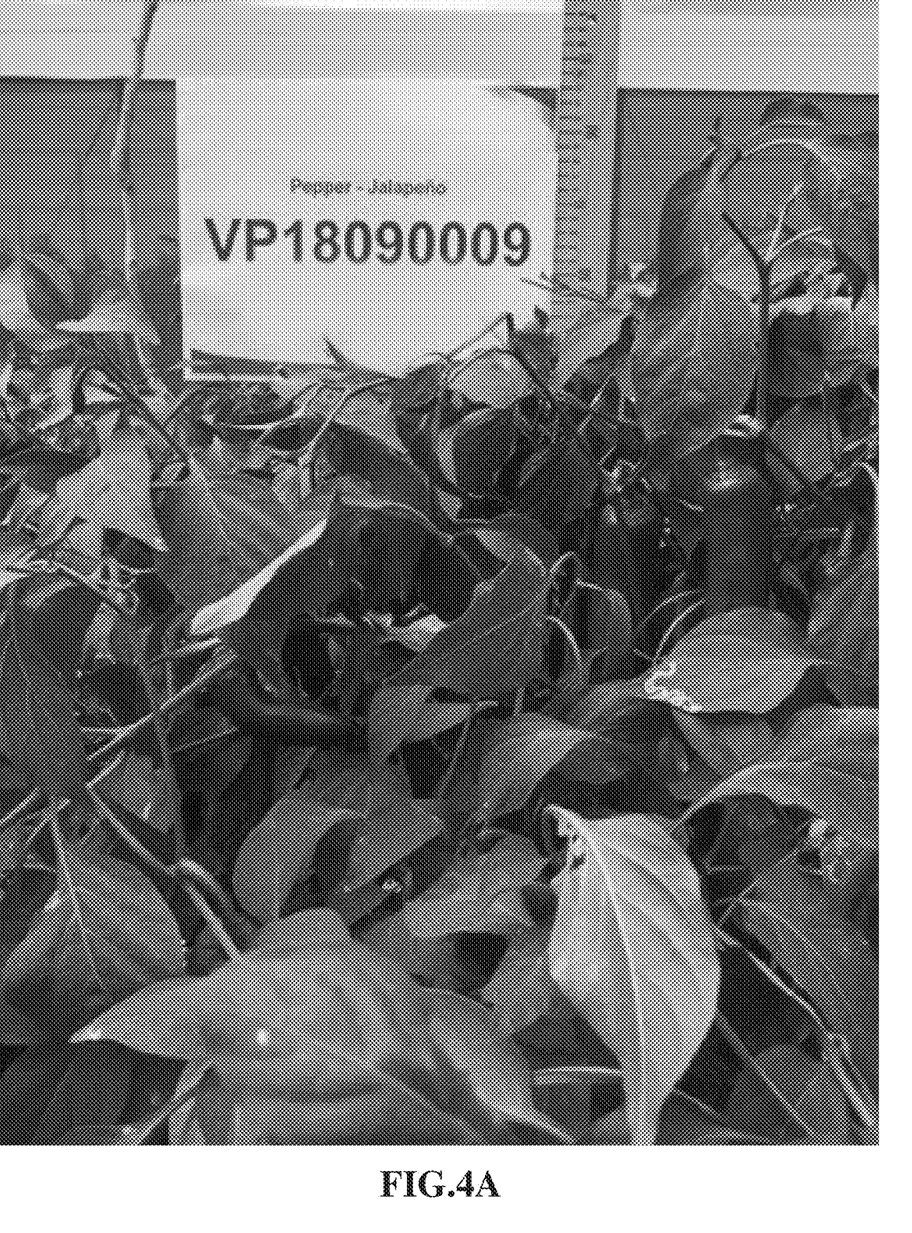
FIG. 4A shows the upper shoots of plants of hybrid pepper 'VP18090009' ("PANTERA") with several fruit visible.

Hybrid pepper 'VP18090009' is a Jalapeno-type hot pepper with extra-large, moderately triangular pungent fruits that are green prior to maturity and red at maturity. Hybrid pepper 'VP18090009' has an indeterminate growth habit and a tall plant height. This results in continuous production of a high number of flowers during the growth of the plant, which results in a high amount of fruit. Additionally, the extra-large fruits of hybrid pepper 'VP18090009' are uniform in size throughout the plant, making this a very attractive hybrid for fresh market. Hybrid pepper 'VP18090009' is the result of numerous generations of plant selections from its parent lines and exhibits vigorous growth, tall plant height, as well as large and uniform fruit size. FIG. 1A shows flowers of hybrid pepper 'VP18090009'. FIG. 2 shows the upper shoot of a plant of hybrid pepper 'VP18090009' ("PANTERA") with fruit. FIG. 3A shows immature fruit of hybrid pepper 'VP18090009'. FIG. 3B shows mature fruit of hybrid pepper 'VP18090009'. FIG. 4A shows the upper shoots of plants of hybrid pepper 'VP18090009' ("PANTERA") with several fruit visible.

Hybrid pepper 'VP18090009' has shown uniformity and stability for the traits, within the limits of environmental influence for the traits. The hybrid has been increased with continued observation for uniformity. No variant traits have been observed or are expected in hybrid pepper 'VP18090009'.

Objective Description of the Hybrid Pepper 'VP18090009'

Hybrid pepper 'VP18090009' was tested for three years in vegetable production environments in Mexico and USA. The terminology and descriptors used in this section are in line with the descriptors of the "UPOV Guidelines for the Conduct of Tests for Distinctness, Uniformity, and Stability", or the "Test Guidelines" for *Capsicum annuum* L. The "Test Guidelines" indicate reference varieties for the descriptors or characteristics that are included in the list. The terminology and descriptors used in these tables are in line with the official terminology as of the filing date, and are thus clear for a person skilled in the art.

Hybrid pepper 'VP18090009' has the following morphologic and other characteristics:

Type: Hot Pepper, Jalapeno
Plant:
  Seedling: Anthocyanin coloration of hypocotyl: Absent
  Shortened internode (in upper part): Absent
  Habit: Indeterminate (continuous production of flowers)
  Peduncle attitude: Semi-drooping
  Height (at maturity): 80-90 cm
  Time of maturity: Early
Fruit:
  Size class: Extra-large
  Length: 4.8-5.5 inches on average; 4-5 inches at top of the plant
  Diameter: 1.5 inches
  Shape: Long to long bullet
  Shape in longitudinal section: Moderately triangular
  Color before maturity: Green
  Color at maturity: Red
  Number of locules: Predominantly four and more
  Cracking: None
  Capsaicin in placenta: Present
  Pungency: High
Disease and Pest Resistances:
  Tobamovirus (Tobacco Mosaic Virus) (TMV) pathotype $P_0$: Moderately susceptible
  Tobamovirus (Pepper Mild Mottle Virus) (PMMoV) pathotype $P_{1-2}$: Moderately susceptible
  Tobamovirus (Pepper Mild Mottle Virus) (PMMoV) pathotype $P_{1-2-3}$: Moderately susceptible
  Potato Virus Y (PVY) pathotype $P_0$: Moderately susceptible Comparison to Other Pepper Variety Table 1 below compares characteristics of hybrid pepper 'VP18090009' with the pepper variety 'Mixteco' (unpatented). Column 1 lists the characteristics, column 2 shows the characteristics for hybrid pepper 'VP18090009', and column 3 shows the characteristics for pepper variety 'Mixteco'. The comparison of hybrid pepper 'VP18090009' with pepper variety 'Mixteco' was conducted in several environments in Mexico. Briefly, hybrid pepper 'VP18090009' exhibits taller and more vigorous plants and produces larger fruit when compared to 'Mixteco'. Specifically, hybrid pepper 'VP18090009' exhibits about 20 centimeters more in plant height than Mixteco which is an indication of improved plant vigor.

TABLE 1

| Characteristic | 'VP18090009' | 'Mixteco' |
| --- | --- | --- |
| Plant height | 80-90 cm (Tall) | 50-60 cm (Compact/intermediate) |
| Fruit size class | Extra-large | Large |
| Fruit length | 4.8-5.5 inches | 4.4-4.7 inches |
| Fruit diameter | 1.5 inches | 1.3-1.4 inches |
| Fruit shape at blossom end | Pointier | Less pointy |

Figure 1B:
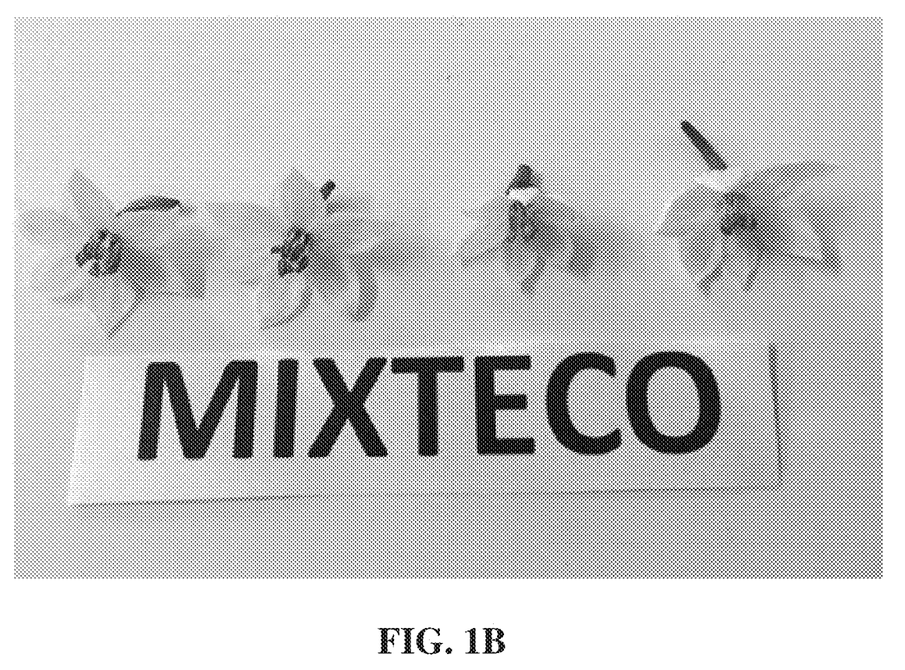
Figure 4B:
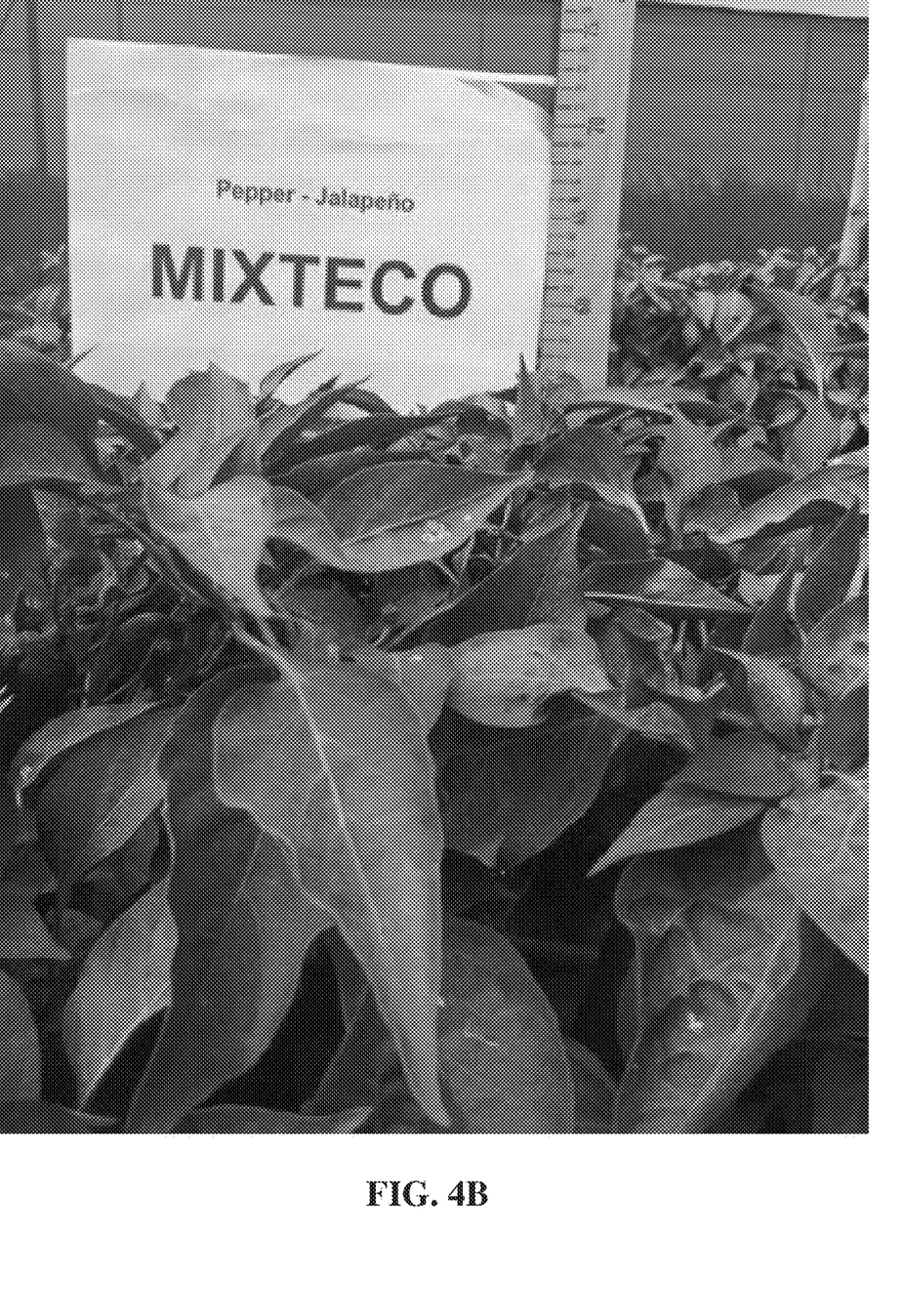
FIG. 4B shows the upper shoots of plants of pepper variety 'Mixteco' with few fruit visible.

FIGS. 1A-1B show a comparison of the flowers of hybrid pepper 'VP18090009' (FIG. 1A) with those of pepper variety 'Mixteco' (FIG. 1B). FIGS. 4A-4B show a comparison of the plant height and fruit load of upper shoots of hybrid pepper 'VP18090009' with those of pepper variety 'Mixteco'. FIG. 4A shows the upper shoots of plants of hybrid pepper 'VP18090009' ("PANTERA") with several fruit visible. FIG. 4B shows the upper shoots of plants of pepper variety 'Mixteco' with few fruit visible.

Table 2 below compares characteristics of hybrid pepper 'VP18090009' with the pepper varieties 'Tzotzil', 'Orizaba', and 'Pánuco' over four trials in two years under open field culture in Jalisco, Mexico. Column 1 lists the characteristics, columns 2 and 4 show the characteristics of hybrid pepper variety 'VP18090009', and columns 3 and 5 show the characteristics of pepper varieties 'Tzotzil', 'Orizaba', and 'Pánuco'. Trial numbers, locations, and evaluation times are noted in rows 1 and 10, above their respective data. Briefly, hybrid pepper 'VP18090009' exhibits higher yield due to heavier fruit when compared to pepper varieties 'Tzotzil', 'Orizaba', and 'Pánuco', and no fruit cracking. Specifically, hybrid pepper 'VP18090009' exhibits 20 grams more weight per fruit than pepper variety 'Tzotzil', at least 4.2 grams more weight per fruit than pepper variety 'Orizaba', and 26 grams more weight per fruit than pepper variety 'Pánuco'.

TABLE 2

|  | Trial 1: Juchitlan, Jalisco Evaluated in July, Year 1 | | Trial 2: Mascota, Jalisco Evaluated in October, Year 1 | |
| --- | --- | --- | --- | --- |
| Variety | 'VP18090009' | 'Tzotzil' | 'VP18090009' | 'Orizaba' |
| Maturity | Early | Early | Early | Early |
| Fruit shape | Long bullet | Long | Long | Long |
| Cracking | No | Light | No | Light |
| Pungency | High | Medium | High | High |
| Fruit Size (g) | 100 | 80 | 83.7 | 75.8 |
| Fruit Size (# × # × # inches) | 4.5 × 1.2 × 0.9 | 4.5 × 1.2 × 0.9 | 5 × 1.2 × 0.9 | 5 × 1.2 × 0.9 |
| First cut yield (ton/ha) | 12.6 | 8.05 | 24.8 | 17.4 |
|  | Trial 3: Juchitlan, Jalisco Evaluated in July, Year 1 | | Trial 4: Mascota, Jalisco Evaluated in November, Year 2 | |
| Variety | 'VP18090009' | 'Pánuco' | 'VP18090009' | 'Orizaba' |
| Maturity | Early | Early | Early | Early |
| Fruit shape | Long bullet | Long sharp | Long | Long |
| Cracking | No | No | No | Light |
| Pungency | High | Medium | High | High |
| Fruit Size (g) | 100 | 74 | 80 | 75.8 |
| Fruit Size (# × # × # inches) | 4.5 × 1.2 × 0.9 | 4.5 × 1.2 × 0.9 | 5 × 1.2 × 0.9 | 5 × 1.2 × 0.9 |
| First cut yield (ton/ha) | 12.6 | 8.87 | 19.2 | 12.88 |

Further Embodiments

This disclosure also is directed to methods for producing a pepper plant by crossing a first parent pepper plant with a second parent pepper plant wherein either the first or second parent pepper plant is a hybrid pepper plant of 'VP18090009'. Further, both first and second parent pepper plants can come from the hybrid pepper 'VP18090009'. All plants produced using hybrid pepper 'VP18090009' as a parent are within the scope of this disclosure, including plants derived from hybrid pepper 'VP18090009'. Plants derived from hybrid pepper 'VP18090009' may be used, in certain embodiments, for the development of new pepper varieties. By selecting plants having one or more desirable traits, a plant derived from hybrid pepper 'VP18090009' is obtained which possesses some of the desirable traits of the hybrid as well as potentially other selected traits.

The development of new varieties using one or more starting varieties is well known in the art. In accordance with this disclosure, novel varieties may be created by crossing hybrid pepper 'VP18090009' followed by multiple generations of breeding according to such well known methods. New varieties may be created by crossing with any second plant. In selecting such a second plant to cross for the purpose of developing novel lines, it may be desired to choose those plants which either themselves exhibit one or more selected desirable characteristics or which exhibit the desired characteristic(s) when in hybrid combination. Once initial crosses have been made, inbreeding and selection take place to produce new varieties. For development of a uniform line, often five or more generations of selfing and selection are involved.

It is preferred to breed for a combination of desirable plant characteristics and resistances to create a single variety or hybrid containing an improved combination of desirable traits from the parental germplasm. The development of commercial pepper hybrids relates to the development of pepper parental lines, the crossing of these lines, and the evaluation of the crosses. Hybrid varieties offer multiple advantages, including a combination of desirable dominant and recessive traits from a set of inbred parents. Pedigree breeding and recurrent selection breeding methods are used to develop cultivars from breeding populations. Breeding programs combine desirable traits from two or more varieties or various broad-based sources into breeding pools from which lines are developed by selfing and selection of desired phenotypes. The new lines are crossed with other lines and the hybrids from these crosses are evaluated to determine which have the desirable characteristics.

Gene Conversions

When the terms "pepper plant", "hybrid", "cultivar", or "pepper line" are used in the context of the present invention, this also includes any gene conversions of that variety. The term "gene converted plant" as used herein refers to those pepper plants which are developed by backcrossing, genetic engineering, or mutation, where essentially all of the desired morphological and physiological characteristics of a variety are recovered in addition to the one or more genes transferred into the variety via the backcrossing technique, genetic engineering, or mutation. Backcrossing methods can be used with the present invention to improve or introduce a characteristic into the variety. The term "backcrossing" as used herein refers to the repeated crossing of a hybrid progeny back to the recurrent parent, i.e., backcrossing 1, 2, 3, 4, 5, 6, 7, 8, 9, or more times to the recurrent parent. The parental pepper plant which contributes the gene for the desired characteristic is termed the "nonrecurrent" or "donor parent." This terminology refers to the fact that the nonrecurrent parent is used one time in the backcross protocol and therefore does not recur. The parental pepper plant to which the gene or genes from the nonrecurrent parent are transferred is known as the recurrent parent, as it is used for several rounds in the backcrossing protocol (Poehlman & Sleper (1994) and Fehr (1993)). In a typical backcross protocol, the original variety of interest (recurrent parent) is crossed to a second variety (nonrecurrent parent) that carries the gene of interest to be transferred. The resulting progeny from this cross are then crossed again to the recurrent parent and the process is repeated until a pepper plant is obtained where essentially all of the desired morphological and physiological characteristics of the recurrent parent are recovered in the converted plant, in addition to the transferred gene from the nonrecurrent parent.

The selection of a suitable recurrent parent is an important step for a successful backcrossing procedure. The goal of a backcross protocol is to alter or substitute a trait or characteristic in the original line. To accomplish this, a gene of the recurrent variety is modified or substituted with the desired gene from the nonrecurrent parent, while retaining essentially all of the rest of the desired genetic, and therefore the desired physiological and morphological, constitution of the original line. The choice of the particular nonrecurrent parent will depend on the purpose of the backcross. One of the major purposes is to add some commercially desirable, agronomically important trait to the plant. The exact backcrossing protocol will depend on the characteristic or trait being altered, which will determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many gene traits have been identified that are not regularly selected in the development of a new line but that can be improved by backcrossing techniques. Examples of these traits include, but are not limited to, male sterility, modified fatty acid metabolism, modified carbohydrate metabolism, herbicide resistance, resistance for bacterial, fungal, or viral disease, insect resistance, enhanced nutritional quality, industrial usage, yield stability, and yield enhancement. These genes are generally inherited through the nucleus. Several of these gene traits are described in U.S. Pat. Nos. 5,777,196, 5,948,957, and 5,969,212.

Tissue Culture

As used herein, the term "tissue culture" indicates a composition containing isolated cells of the same or a different type or a collection of such cells organized into parts of a plant. Exemplary types of tissue cultures are protoplasts, calli, meristematic cells, and plant cells that can generate tissue culture that are intact in plants or parts of plants, such as leaves, pollen, embryos, roots, root tips, anthers, pistils, flowers, seeds, petioles, suckers, and the like. Means for preparing and maintaining plant tissue culture are well known in the art. By way of example, a tissue culture containing organs has been used to produce regenerated plants. U.S. Pat. Nos. 5,959,185, 5,973,234, and 5,977,445 describe certain techniques, which may be used.

Tissue culture of pepper can be used for the in vitro regeneration of pepper plants. Tissues cultures of various tissues of pepper and regeneration of plants therefrom are well-known and published. By way of example, tissue cultures, some comprising organs to be used to produce regenerated plants, as well as regeneration by somatic embryogenesis, have been described in Gammoudi, et al., In Vitro Cellular & Developmental Biology—Plant, 54, 145-153 (2018); Kothari, et al., Biotechnology Advances, 28:1, 34-48 (2010); Ochoa-Alejo and Ramirez-Malagon, In Vitro Cellular & Developmental Biology—Plant, 37, 701-729 (2001); Irikova, et al., Acta Physiologiae Plantarum, 33, 1559-1570 (2011); Ochoa-Alejo and Ireta-Moreno, Scientia Horticulturae, 42:1-2, 21-28 (1990); Gunay and Rao, Plant Science Letters, 11:3-4, 365-372 (1978). It is clear from the literature that these methods of obtaining plants are "conventional" in the sense that they are routinely successfully used. Thus, another aspect of this disclosure is to provide cells which upon growth and differentiation produce pepper plants having the physiological and morphological characteristics of hybrid pepper 'VP18090009'.

Additional Breeding Methods

The hybrid pepper of the disclosure can also be used for transformation where exogenous genes are introduced and expressed by the cultivar of the disclosure. Genetic variants of 'VP18090009' created either through traditional breeding methods or through transformation of hybrid pepper 'VP18090009' by any of a number of protocols known to those of skill in the art are intended to be within the scope of this disclosure.

Mutations for use in mutation breeding can be induced in plants by using mutagenic chemicals such as ethyl methane sulfonate (EMS), by irradiation of plant material with gamma rays or fast neutrons, or by other means. The resulting nucleotide changes are random, but in a large collection of mutagenized plants the mutations in a gene of interest can be readily identified by using the TILLING (Targeting Induced Local Lesions IN Genomes) method (McCallum et al. (2000) Targeted screening for induced mutations. Nat. Biotechnol. 18, 455-457, and Henikoff et al. (2004) TILLING. Traditional mutagenesis meets functional genomics. Plant Physiol. 135, 630-636). The principle of this method is based on the PCR amplification of the gene of interest from genomic DNA of a large collection of mutagenized plants in the M2 generation. By DNA sequencing or by looking for point mutations using a single-strand specific nuclease, such as the CEL-I nuclease (Till et al. (2004) Mismatch cleavage by single-strand specific nucleases. Nucleic Acids Res. 32, 2632-2641), the individual plants that have a mutation in the gene of interest are identified. By screening many plants, a large collection of mutant alleles is obtained, each giving a different effect on gene expression or enzyme activity. The gene expression or protein levels can for example be tested by transcript analysis levels (e.g., by RT-PCR) or by quantification of protein levels with antibodies. Plants with the desired reduced gene expression or reduced protein expression are then backcrossed or crossed to other breeding lines to transfer only the desired new allele into the background of the crop wanted.

Genes of interest for use in breeding may also be edited using gene editing techniques including transcription activator-like effector nuclease (TALEN) gene editing techniques, Clustered Regularly Interspaced Short Palindromic Repeat (CRISPR/Cas9) gene editing techniques, and/or zinc-finger nuclease (ZFN) gene editing techniques. For this, transgenic plants are generated expressing one or more constructs targeting the gene of interest. These constructs may include, without limitation, an anti-sense construct, an optimized small-RNA construct, an inverted repeat construct, a targeting construct, a guide RNA construct, a construct encoding a targeting protein, and/or a combined sense-anti-sense construct, and may work in conjunction with a nuclease, an endonuclease, and/or an enzyme, so as to downregulate the expression of a gene of interest.

One of ordinary skill in the art of plant breeding would know how to evaluate the traits of two plant varieties to determine if there is no significant difference between the two traits expressed by those varieties. For example, see Fehr and Walt, Principles of Cultivar Development, p. 261-286 (1987). Thus the disclosure includes hybrid pepper 'VP18090009' progeny pepper plants including a combination of at least two 'VP18090009' traits selected from the combination of traits listed in the Overview of the Hybrid 'VP18090009', so that said progeny pepper plant is not significantly different for said traits than pepper 'VP18090009' as determined at the 5% significance level when grown in the same environmental conditions and/or may be characterized by percent similarity or identity to hybrid pepper 'VP18090009' as determined by SSR markers. Using techniques described herein, molecular markers may be used to identify said progeny plant as a hybrid pepper 'VP18090009' progeny plant. Mean trait values may be used to determine whether trait differences are significant, and preferably the traits are measured on plants grown under the same environmental conditions. Once such a variety is developed its value is substantial since it is important to advance the germplasm base as a whole in order to maintain or improve traits such as yield, disease resistance, pest resistance, and plant performance in extreme environmental conditions.

As used herein, the term "plant" includes plant cells, plant protoplasts, plant cell tissue cultures from which pepper plants can be regenerated, plant calli, plant clumps, and plant cells that are intact in plants or parts of plants, such as leaves, pollen, embryos, cotyledons, hypocotyl, roots, root tips, anthers, pistils, flowers, ovules, seeds, stems, and the like.

The use of the terms "a," "an," and "the," and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

While a number of exemplary aspects and embodiments have been discussed above, those of skill in the art will recognize certain modifications, permutations, additions, and sub-combinations thereof. It is therefore intended that the following appended claims and claims hereafter introduced are interpreted to include all such modifications, permutations, additions, and sub-combinations as are within their true spirit and scope.

DEPOSIT INFORMATION

A deposit of at least 625 seeds of the hybrid pepper variety 'VP18090009' was made with the American Type Culture Collection (ATCC), P.O. Box 1549, Manassas, VA 20108 USA, and assigned ATCC Number PTA-127283. The seeds deposited with the ATCC on Mar. 22, 2022 were obtained from the seed of the variety maintained by VoloAgri Group, Inc., 12050 County Road 97, Woodland, California 95695, USA since prior to the filing date of the application. Access to this deposit will be available during the pendency of this application to persons determined by the Commissioner of Patents and Trademarks to be entitled thereto under 37 C.F.R. § 1.14 and 35 U.S.C. § 122. Upon issuance, the Applicant will make the deposit available to the public consistent with all of the requirements of 37 C.F.R. § 1.801-1.809. This deposit of the hybrid pepper variety 'VP18090009' will be maintained in the ATCC, which is a public depository, for a period of 30 years, or at least 5 years after the most recent request for a sample of the deposit, or for the effective life of the patent, whichever is longer, and will be replaced if it becomes nonviable during that period. Applicant has no authority to waive any restrictions imposed by law on the transfer of biological material or its transportation in commerce. Applicant does not waive any infringement of rights granted under this patent or under the Plant Variety Protection Act (7 USC 2321 et seq.).

The invention claimed is:

1. A seed of hybrid pepper designated as 'VP18090009', representative sample of seed having been deposited under ATCC Accession Number PTA-127283.

2. A pepper plant produced by growing the seed of claim 1.

3. A plant part from the plant of claim 2, wherein said part is a leaf, a fruit, or a cell.

4. The plant part of claim 3, wherein said part is a fruit.

5. A pepper plant having all the physiological and morphological characteristics of the pepper plant of claim 2.

6. A plant part from the plant of claim 5, wherein said part is a leaf, a fruit, or a cell.

7. The plant part of claim 6, wherein said part is a fruit.

8. A protoplast produced from the plant of claim 2, wherein said protoplast is produced from a part of the plant selected from the group consisting of root, root tip, meristematic cell, stem, hypocotyl, petiole, cotyledon, leaf, and fruit.

9. A tissue or cell culture produced from protoplasts or cells from the plant of claim 2, wherein said cells or protoplasts are produced from a plant part selected from the group consisting of root, root tip, meristematic cell, stem, hypocotyl, petiole, cotyledon, leaf, and fruit.

10. A pepper plant regenerated from the tissue or cell culture of claim 9, wherein the plant has all of the morphological and physiological characteristics of a pepper plant produced by growing hybrid pepper seed designated as 'VP18090009', representative sample of seed having been deposited under ATCC Accession Number PTA-127283.

11. A method of producing a 'VP18090009'-derived pepper seed, comprising the steps:
   a) crossing a hybrid pepper designated as 'VP18090009' with a second pepper plant or self-pollinating a hybrid pepper plant designated as 'VP18090009'; and
   b) whereby seed of a 'VP18090009'-derived pepper plant forms.

12. The method of claim 11, further comprising the steps of:
   c) crossing a plant grown from 'VP18090009'-derived pepper seed with a second pepper plant or self-pollinating a plant grown from a 'VP18090009'-derived pepper seed to yield additional 'VP18090009'-derived pepper seed;
   d) growing the additional 'VP18090009'-derived pepper seed of step (c) to yield additional 'VP18090009'-derived pepper plants; and
   e) repeating steps (c) and (d) for an additional 3-10 generations to generate further 'VP18090009'-derived pepper plants.

13. A method of vegetatively propagating a plant of hybrid pepper 'VP18090009', the method comprising the steps of:
   a) collecting tissue capable of being propagated from a plant of hybrid pepper 'VP18090009', representative sample of seed having been deposited under ATCC Accession Number PTA-127283;
   b) cultivating the tissue to obtain proliferated shoots; and
   c) rooting the proliferated shoots to obtain rooted plantlets.

14. The method of claim 13, further comprising step (d) growing plants from the rooted plantlets.

15. A method of producing a pepper fruit, said method comprising growing the plant of claim 2 until it sets at least one fruit, and harvesting the fruit.

* * * * *